United States Patent [19]

Yamada et al.

[11] Patent Number: 4,885,274

[45] Date of Patent: Dec. 5, 1989

[54] PERFUME COMPOSITION

[75] Inventors: Nobuo Yamada; Toyohiko Kobayashi, both of Yokohama, Japan

[73] Assignee: Takasago Perfumery Co., Ltd., Tokyo, Japan

[21] Appl. No.: 139,253

[22] PCT Filed: Mar. 5, 1987

[86] PCT No.: PCT/JP87/00140

§ 371 Date: Nov. 23, 1987

§ 102(e) Date: Nov. 23, 1987

[87] PCT Pub. No.: WO88/06435

PCT Pub. Date: Sep. 7, 1988

[51] Int. Cl.[4] .................... A61K 7/46

[52] U.S. Cl. .................... 512/16; 568/326

[58] Field of Search .................... 568/326; 512/16

[56] References Cited

U.S. PATENT DOCUMENTS

| | | | |
|---|---|---|---|
| 4,284,819 | 8/1981 | Sprecker et al. | 568/326 |
| 4,541,948 | 9/1985 | Joulain | 568/326 |

FOREIGN PATENT DOCUMENTS

| | | | |
|---|---|---|---|
| 1543064 | 6/1971 | Fed. Rep. of Germany | 512/16 |
| 45-336 | 1/1970 | Japan | 512/16 |

*Primary Examiner*—James H. Reamer

*Attorney, Agent, or Firm*—Frishauf, Holtz, Goodman & Woodward

[57] ABSTRACT

The perfume composition containing 4- (or 5-)-acyl-1,1-(or 3,3-)-[a] compound, which is a novel compound expressed by the formula I, has noble musk fragrance. In addition, this perfume composition has characteristics that it is excellent in both quality and strength of the fragrance, of high safety and capable of being manufactured with low costs.

11 Claims, 7 Drawing Sheets

PERFUME COMPOSITION

FIELD OF TECHNOLOGY

This invention relates to a perfume composition or, more particularly, relates to a perfume composition containing a novel compound represented by the formula (I) given below [in the formula, $R_1$ is a methyl or ethyl group and either one of $R_2$ and $R_3$ is a methyl group, the other being a hydrogen atom].

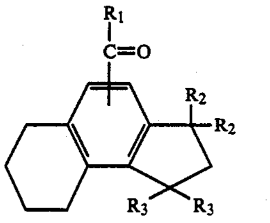

(1)

This perfume composition can be used effectively in soaps, liquid scents, cosmetics, room aromatics, masking agents and the like.

BACKGROUND TECHNOLOGY

In view of the extreme expensiveness and unstable supply of natural musk obtained from a musk deer, works have been undertaken intensively from old times to develop compounds having musk-like tone of fragrance and a large number of compounds have been discovered including those belonging to the types of nitro-musks, indan musks, Tetralin musks, macrocyclic musks and the like.

In recent years, however, several of these compounds have become banned for use in soaps, cosmetics and the like in respect of the safety concern. Therefore, it is desired to have advent of a compound having musk-like tone of fragrance but less problems in safety. As such a compound, compounds having a skeleton of cyclopentanaphthalene are known and disclosures are already given for

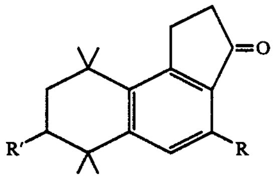

in German Pat. No. 2,114,216 and for

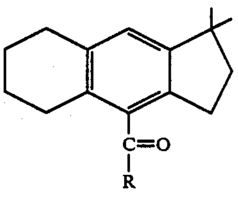

in Japanese Patent Publication 42-6491 while they are each not satisfactory in respect of the quality and strength of the fragrance although they have no problem in respect of safety.

Accordingly, the object of the present invention is to provide a compound of musk-like fragrance having a skeleton of cyclopentanaphthalene with high safety, low costs for manufacturing and fragrance excellent in both of quality and strength.

DISCLOSURE OF THE INVENTION

In the course of the comparative investigations for the synthetic methods and fragrance characteristics of a large number of compounds having a skeleton of cyclopentanaphthalene, the inventors have arrived at a discovery that acylation of a mixture composed of 1,1-dimethyl-2,3,5,6,7,8-hexahydro-1H-cyclopenta[b]-naphthalene (referred to as the 1,1-[b] compound hereinbelow), 1,1-dimethyl-2,3,6,7,8,9-hexahydro-1H-cyclopenta[a]naphthalene (referred to as the 1,1-[a] compound hereinbelow) and 3,3-dimethyl-1,2,6,7,8,9-hexahydro-1H-cyclopenta[a]naphthalene (referred to as the 3,3-[a] compound hereinbelow) produced by the cyclization reaction of Tetralin and isoprene gives a mixture composed of the 4-acyl-1,1-[b] compound and 4-(or 5-)acyl-1,1-(or 3,3-)-[a] compound, which in itself has only ionone-like weak musk fragrance but is capable of giving a perfume composition having unexpectedly strong and noble musk fragrance by removing the 4-acyl-1,1-[b] compound, which is a known compound, by column chromatography and that the entity of the musk fragrance is the 4-(or 5-)acyl-1,1-(or 3,3-)-[a] compound, which is a novel compound, leading to completion of the present invention.

Namely, the present invention relates to a perfume composition containing the 4-(or 5-)-acyl-1,1-(or 3,3-)-[a] compound represented by the formula

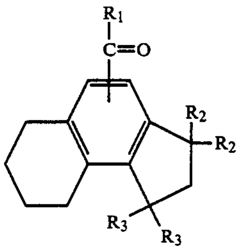

[I]

[in the formula, $R_1$ is a methyl group or ethyl group and either one of $R_2$ and $R_3$ is a methyl group, the other being a hydrogen atom].

THE BEST MODE TO PRACTICE THE INVENTION

Figure 1:
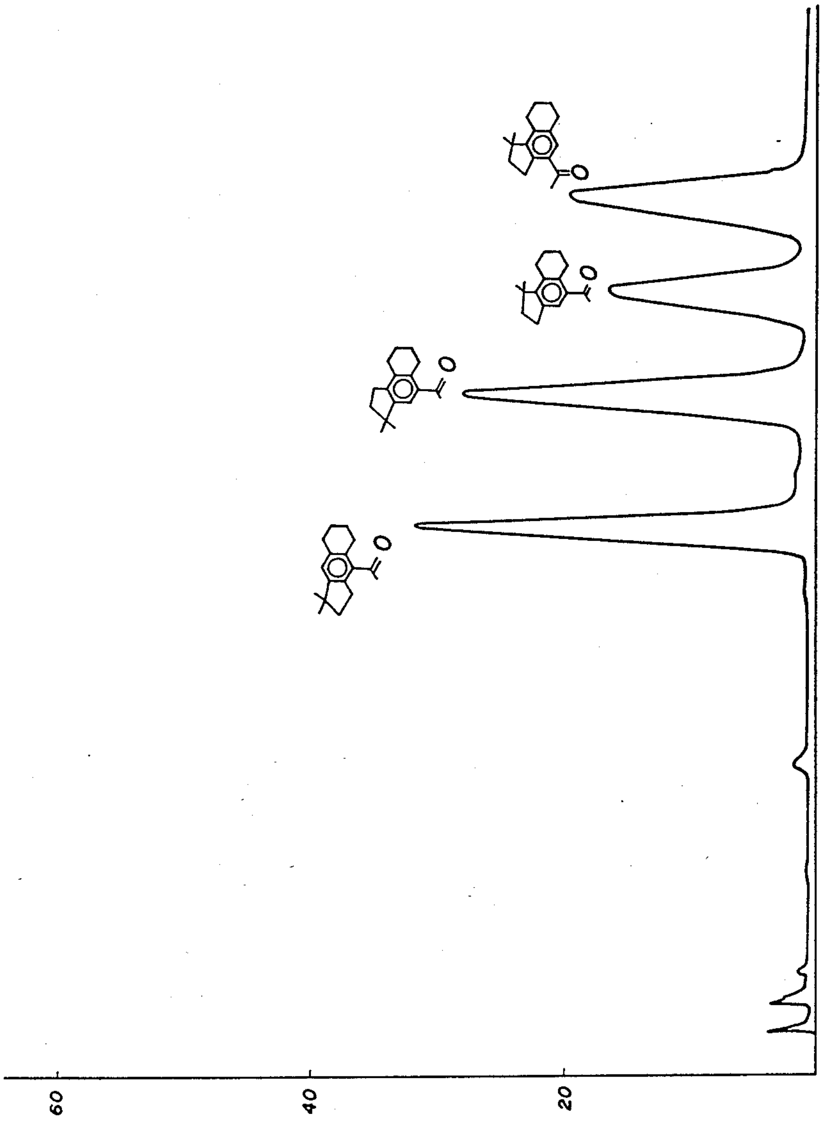
FIG. 1 is a gas chromatogram of the acylated mixture obtained in Preparatory Example 2.

In order to obtain the perfume composition of the present invention, Tetralin is subjected to a cycloaddition of isoprene, as is shown by the following reaction equation, according to a known method (Japanese Patent Publication 42-6491, Japanese Patent Publication 60-20364, and others) to give a mixture composed of the 1,1-[b] compound, 1,1-[a] compound and 3,3-[a] compound (they are produced in a proportion of approximately 32:40:28) which is further acylated into a mixture of the 4-acyl-1,1-[b] compound the 4-(5-)-acyl-1,1-(or 3,3-)-[a] compound. (Note that the 4-acyl-3,3-[a] compound is scarcely formed).

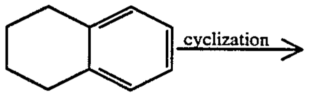

Tetralin

+

Isoprene

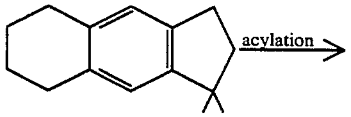

1,1-[b] compound

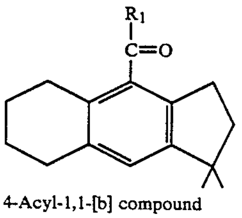

4-Acyl-1,1-[b] compound

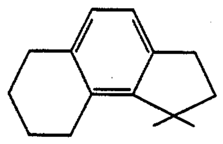

1,1-[a] compound

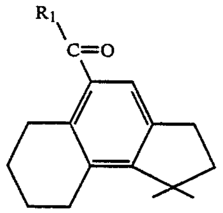

5-Acyl-1,1-[a] compound

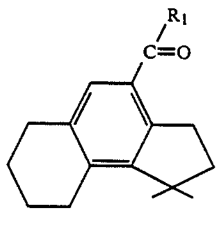

4-Acyl-1,1-[a] compound

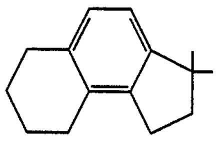

3,3-[a] compound

-continued

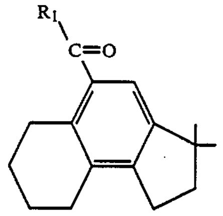

5-Acyl-3,3-[a] compound

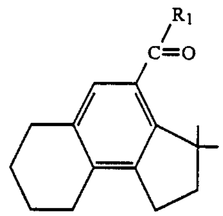

4-Acyl-3,3-[a] compound

The mixture of the acylated compounds can be eluted by the silica gel column chromatography using a mixture of ethyl acetate and n-hexane (1:20) as the eluent in a sequential order of 4-acyl-1,1-[b] compound, 5-acyl-3,3-[a] compound, 5-acyl-1,1-[a] compound and 4-acyl-1,1-[a] compound so that the perfume composition of the present invention can be obtained by removing the 4-acyl-1,1-[b] compound.

In the present invention, the 4-(or 5-)-1,1-(or 3,3-)-[a] compounds can be used either as a mixture or singly after isolation into the individual compounds. When they are used after isolation, the 4-acyl-1,1-[a] compound is the best in both of the quality and strength as a musk fragrance and next comes the 5-acyl-3,3-[a] compound.

Further, the $R_1$ in the acyl groups should preferably be a methyl group or an ethyl group as a musk fragrance and propyl group and higher groups are undesirable due to the ionone-like tone as the musk fragrance.

The perfume composition of the present invention obtained in this manner can be used effectively in soaps, perfumes, cosmetics, airfreshners, masking agents and the like as a safe and high-quality perfume base having musk fragrance and serves to improve and strengthen the fragrance of these products imparting an increased commercial value thereto.

The added amount of the compound represented by the formula [I] in the present invention should be adequately selected in consideration of the object of use and other factors and the added amount in the final product is usually from 0.001 to 10% by weight or, preferably, from 0.01 to 1% by weight. And, it is optional that the perfume composition of the present invention is admixed with conventional auxiliary ingredients such as solvents, surface active agents, germicides, coloring agents and the like.

In the following, the present invention is described in more detail by way of Examples and Reference Examples.

PREPARATORY EXAMPLE 1

Preparation of cyclized mixture.

290 g of Tetralin were admixed with 300 g of a 93% sulfuric acid and chilled at −5° C. A solution prepared by dissolving 61.2 g (0.9M) of isoprene in 290 g of Tetralin was added dropwise thereto at −5° to 0° C. under vigorous agitation over a period of 4 hours. After completion of the dropwise addition, agitation was further continued for additional 1 hour at the same temperature followed by phase separation of the oily layer separated by standing.

The oily layer was successively washed with water, a 5% sodium hydroxide solution and a 5% sodium hydrogen carbonate solution followed by drying with anhydrous sodium sulfate. After removing the unreacted Tetralin by distillation, distillation was performed and the fraction boiling at 89° to 98° C. under 0.3 mmHg was collected to give the cyclized mixture. The yield was 100 g (55.5% of the theoretical yield) and the characteristic parameters were $d_{20}^{20}=0.978$ and $n_D^{20}=1.545$.

This mixture was identified from the results of the gas chromatographic analysis to be composed of the 1,1-[b] compound, 1,1-[a] compound and 3,3-[a] compound approximately in a proportion of 32:40:28.

PREPARATORY EXAMPLE 2

Preparation of acetylated mixture.

50 g of 1,2-dichloroethane are admixed with 31.2 g of aluminum chloride and 21.2 g (0.27M) of acetyl chloride are added thereto dropwise at room temperature over a period of 15 minutes. A solution prepared by dissolving 36.5 g (0.18M) of the mixture obtained in Preparatory Example 1 in 25 g of 1,2-dichloroethane was added thereto dropwise under agitation at room temperature over a period of 30 minutes. After completion of the dropwise addition, agitation was further continued for additional 1 hour and then it was poured into ice water to decompose the catalyst followed by phase separation to take the separated oily layer.

The oily layer was successively washed with water, a 5% sodium hydroxide solution and water followed by drying with anhydrous sodium sulfate. After removing the dichloroethane by distillation, distillation was performed and a fraction boiling at 140° to 142° C. under 0.2 mmHg was collected to give the acetylated mixture. The yield of the thus obtained mixture was 36.3 g (82.0% of the theoretical yield) and the characteristic parameters were $d_{20}^{20;b}=1.047$ and $n_D^{20}=1.557$.

This mixture was identified from the results of the gas chromatographic analysis to be composed of the 4-acetyl-1,1-[b] compound, 5-acetyl-3,3-[a] compound, 5-acetyl-1,1-[a] compound and 4-acetyl-1,1-[a] compound formed approximately in a proportion of 27:29:20:24.

The chromatogram is illustrated in FIG. 1.

PREPARATORY EXAMPLE 3

Preparation of propionylated mixture.

The reaction was performed in the same manner as in Preparatory Example 2 excepting the use of 25 g (0.27M) of propionyl chloride in place of the acetyl chloride in Preparatory Example 2 and the fraction boiling at 147° to 150° C. under 0.1 mmHg was collected by distillation to give 38.1 g (82.6% of the theoretical yield) of the propionylated mixture.

PREPARATORY EXAMPLE 4

Preparation of perfume composition and isolation of the individual ingredients.

25 g of the acetylated mixture obtained in Preparatory Example 2 were dissolved in 50 ml of n-hexane and column chromatography was performed using a silica gel as the stationary phase (6 cm × 120 cm) and ethyl acetate:n-hexane (1:20) as the eluent.

Since the acetylated mixture was eluted out in the sequential order of the 4-acetyl-1,1-[b] compound, 5-acetyl-3,3-[a] compound, 5-acetyl-1,1-[a] compound and 4-acetyl-1,1-[a] compound, a perfume composition could be obtained by removing the 4-acetyl-1,1-[b] compound from the acetylated mixture. Further, each of the individual ingredients was isolated by the second chromatography of the respective fraction rich in the content of the ingredient.

Each of the ingredients as a novel compound has characteristic parameters shown below.

Figure 2:
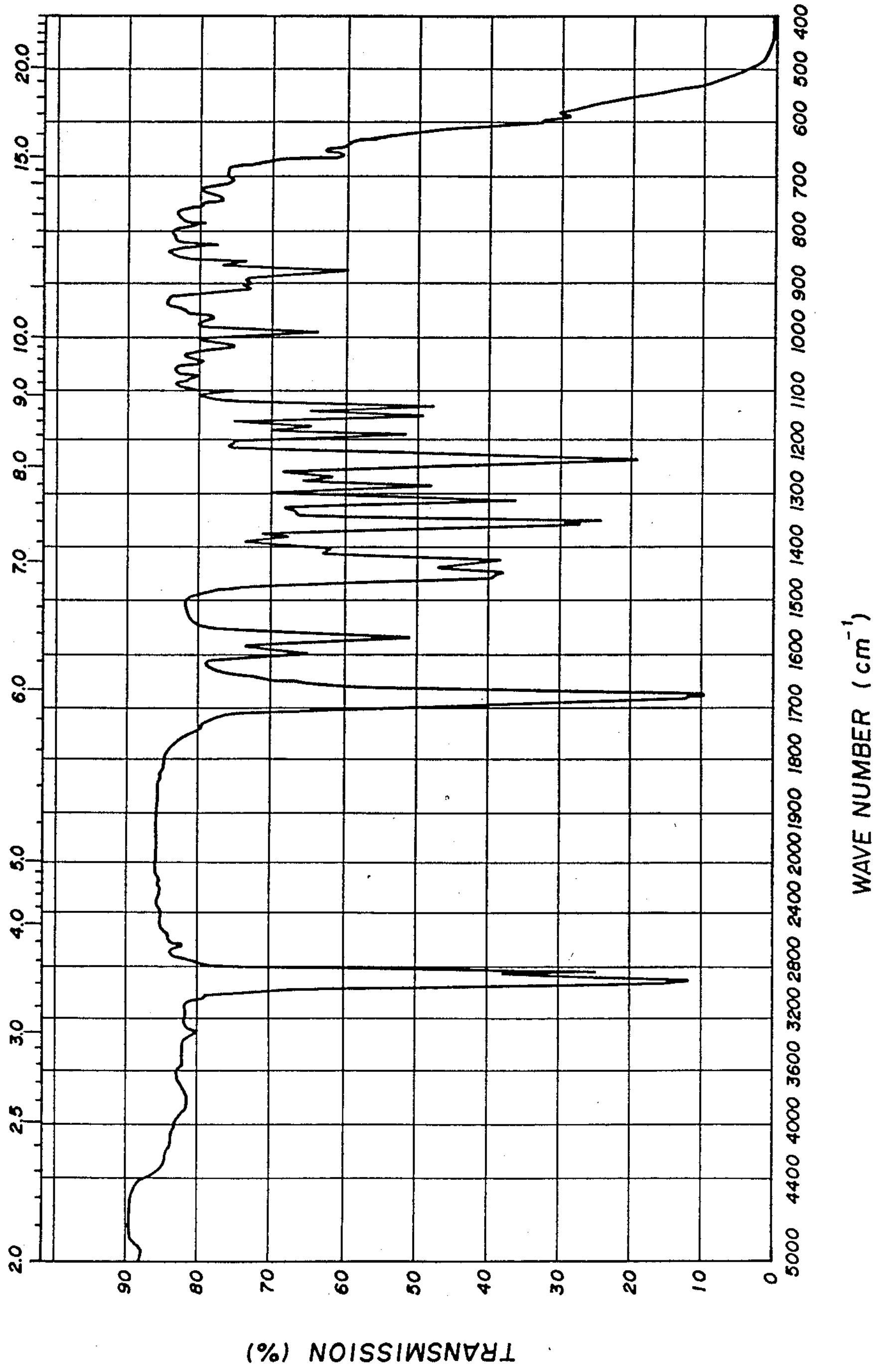
FIG. 2 is an infrared spectrum of the 5-acetyl-3,3-[a] compound obtained in Preparatory Example 4.
Figure 3:
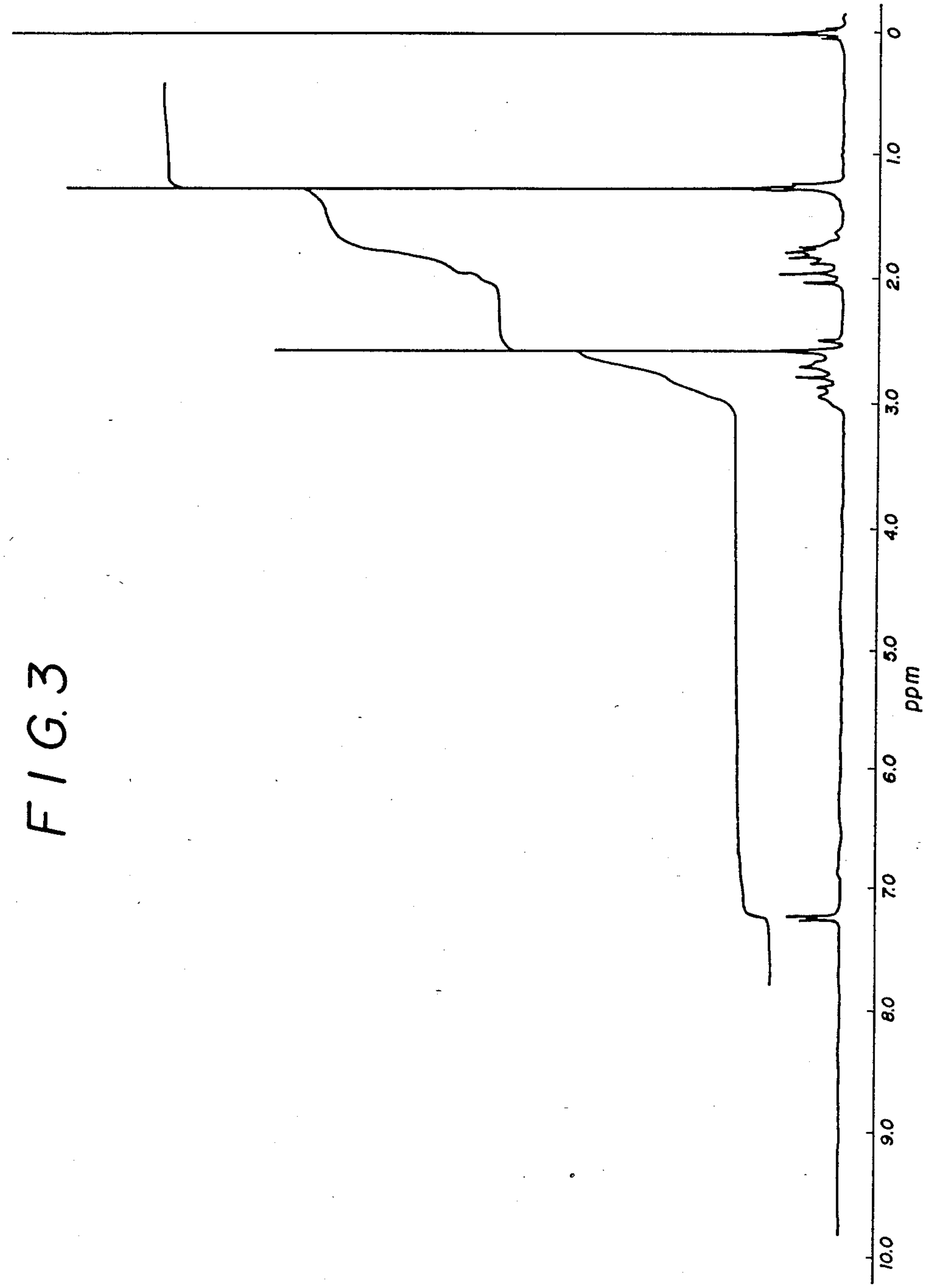
FIG. 3 is an NMR spectrum of the 5-acetyl-3,3-[a] compound obtained in Preparatory Example 4.

5-Acetyl-3,3-[a] compound: $d_{20}^{20}=1.046$; $n_D^{20}=1.556$;

IR (liquid film on NaCl, $cm^{-1}$) 1680 (C=O) (shown in FIG. 2);

NMR ($CDCl_3$, ppm) 1.27 (6H: 3,3-di-$CH_3$), 2.56 (3H: acetyl $CH_3$), 7.24 (H: 4-H), (shown in FIG. 3)

Figure 4:
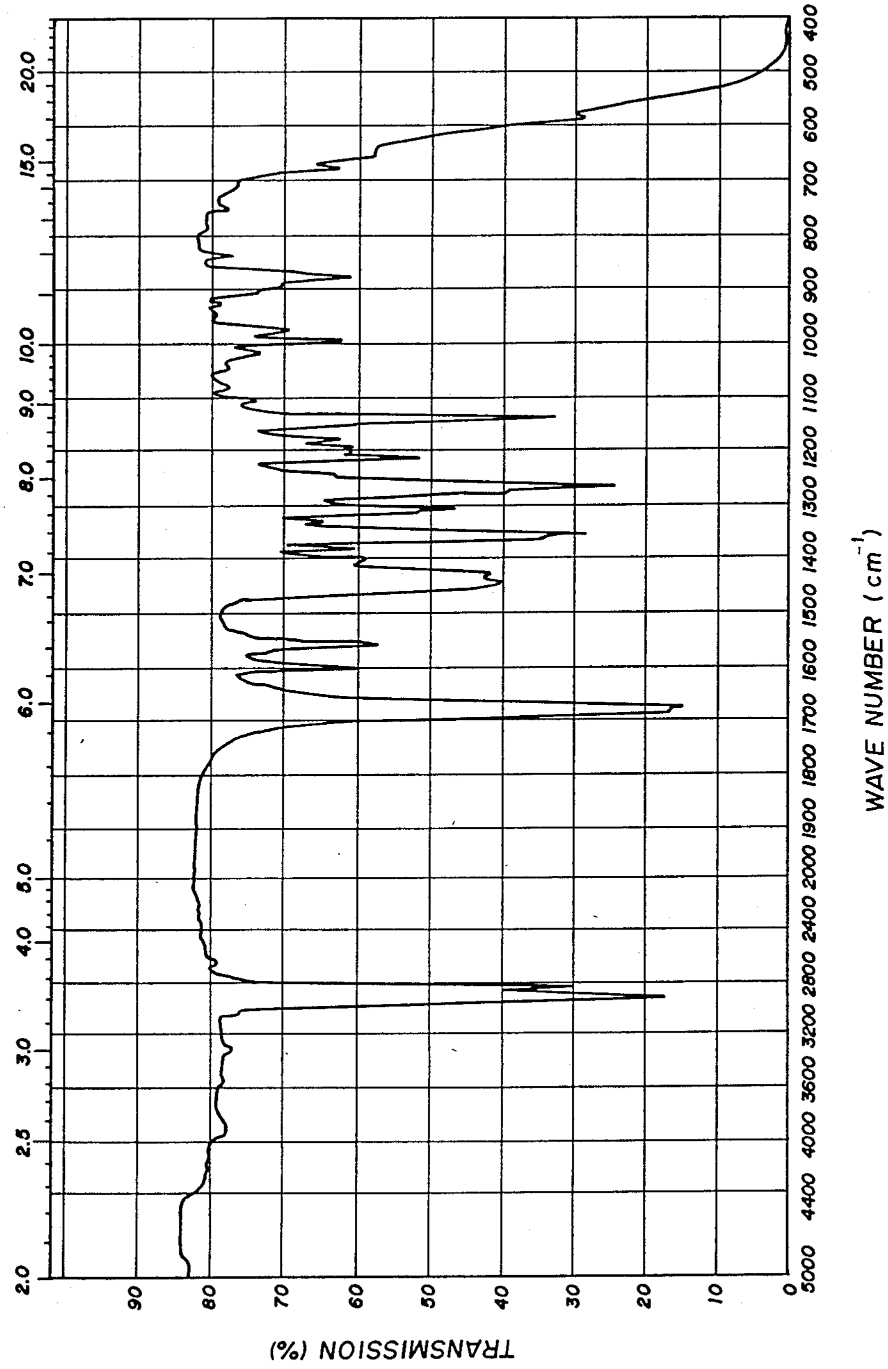
FIG. 4 is an infrared spectrum of the 5-acetyl-1,1-[a] compound obtained in Preparatory Example 4.
Figure 5:
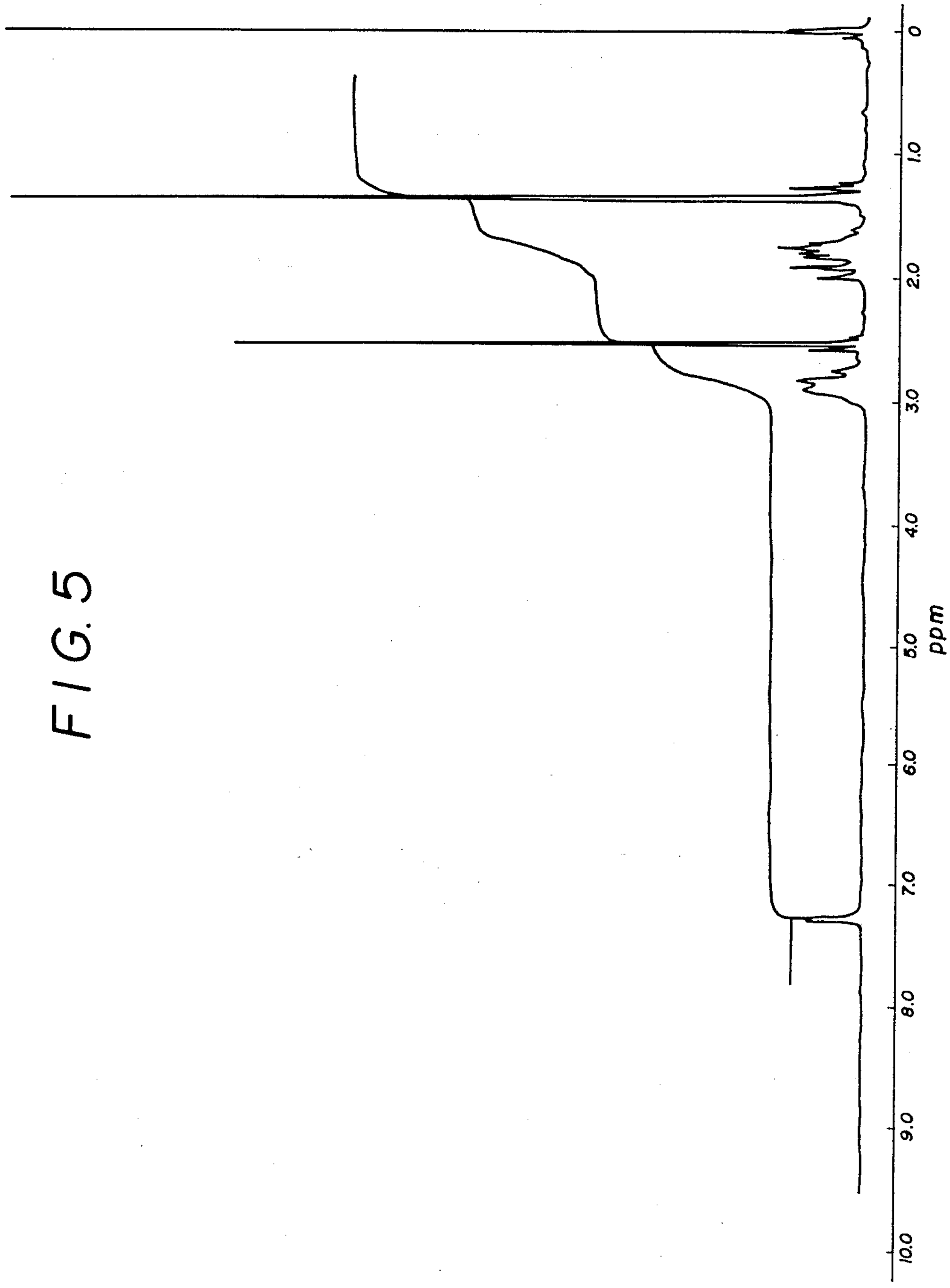
FIG. 5 is an NMR spectrum of the 5-acetyl-1,1-[a] compound obtained in Preparatory Example 4.

5-Acetyl-1,1-[a] compound: $d_{20}^{20}=1.047$; $n_D^{20}=1.557$;

IR (liquid film on NaCl, $cm^{-1}$) 1680 (C=O) (shown in FIG. 4);

NMR ($CDCl_3$, ppm) 1.35 (6H: 1,1-di-$CH_3$), 2.53 (3H: acetyl $CH_3$), 7.26 (H: 4-H), (shown in FIG. 5)

Figure 6:
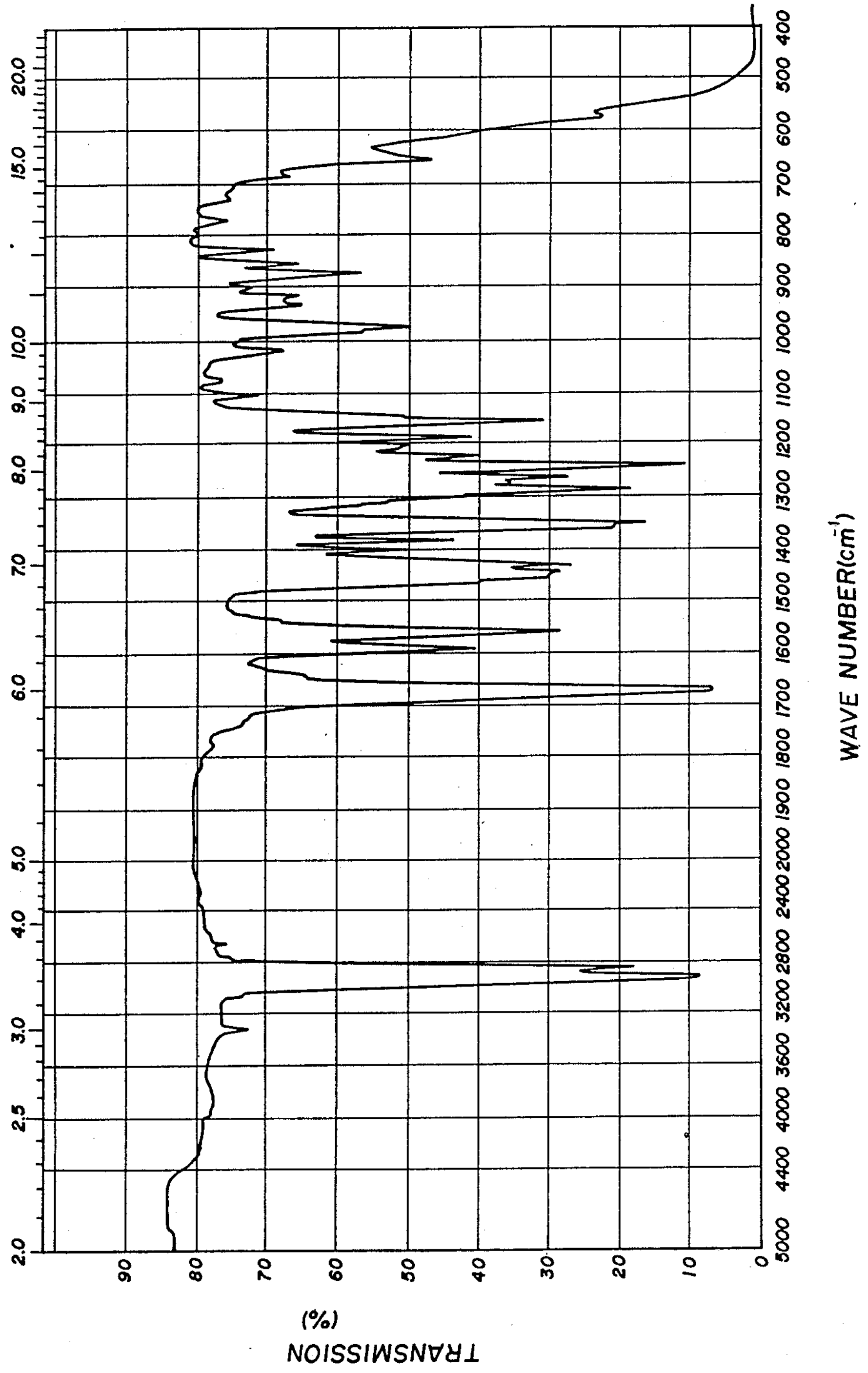
FIG. 6 is an infrared spectrum of the 4-acetyl-1,1-[a] compound obtained in Preparatory Example 4.
Figure 7:
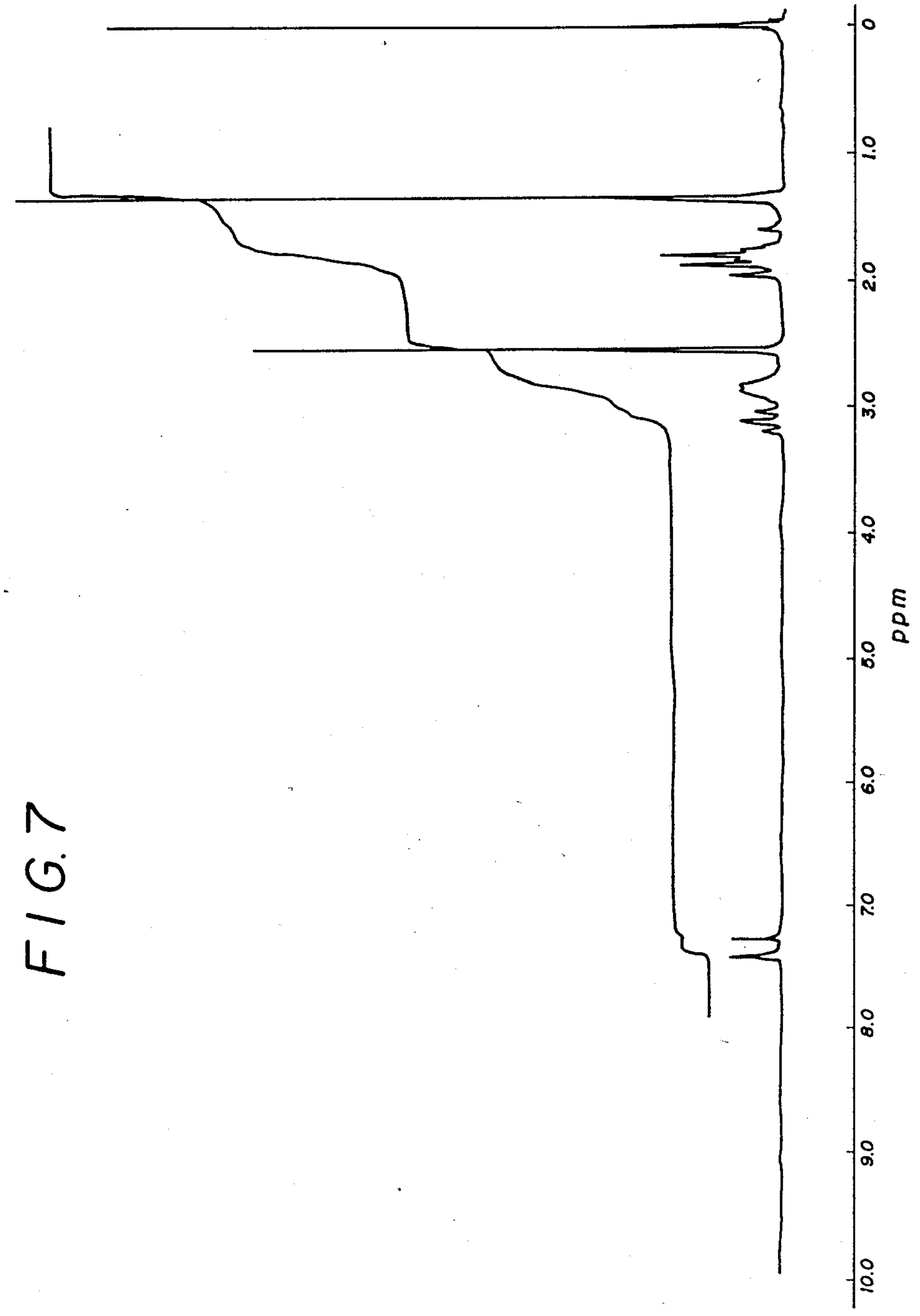
FIG. 7 is an NMR spectrum of the 4-acetyl-1,1-[a] compound obtained in Preparatory Example 4.

4-Acetyl-1,1-[a] compound: $d_{20}^{20}=1.047$; $n_D^{20}=1.557$;

IR (liquid film on NaCl, $cm^{-1}$) 1675 (C=O) (shown in FIG. 6);

NMR ($CDCl_3$, ppm) 1.33 (6H: 1,1-di-$CH_3$), 2.54 (3H: acetyl $CH_3$), 7.42 (H: 5-H), (shown in FIG. 7)

PREPARATORY EXAMPLE 5

Isolation of the individual ingredients from the propionylated mixture.

In the same manner as in Preparatory Example 4 excepting the use of the propionylated mixture obtained in Preparatory Example 3 in place of the acetylated mixture in Preparatory Example 4, the individual ingredients of the 4-propionyl-1,1-[b] compound, 5-propionyl-3,3-[a] compound, 5-propionyl-1,1-[a] compound and 4-propionyl-1,1-[a] compound were isolated.

REFERENCE EXAMPLE 1

Evaluation of fragrance.

Evaluation of fragrance was performed of the acetylated mixture obtained in Preparatory Example 2 and each of the ingredients obtained in Preparatory Example 4 by three expert perfumers. The result are shown in Table 1.

TABLE 1

| | Sample | Threshold value | Odor character |
|---|---|---|---|
| Control | Acetylated mixture | 1/500 | Ionone-like weak musk fragrance |
| Control | 4-Acetyl-1,1-[b] compound | 1/500 | Ionone-like weak musk fragrance |
| Present invention | 5-Acetyl-3,3-[a] compound | 1/10000 | Somewhat strong nitro musk fragrance |
| Present invention | 5-Acetyl-1,1-[a] compound | 1/1000 | Weak musk fragrance |
| Present invention | 4-Acetyl-1,1-[a] compound | 1/100000 | Noble and strong musk fragrance |

As is clear from Table 1, the 4-acetyl-1,1-[a] compound had the highest quality as well as highest strength of the fragrance and the strength thereof was about 200 times of that of the acetylated mixture.

EXAMPLE 1

Application to perfume.

A perfume described below was prepared respectively using the perfume composition obtained in Preparatory Example 4.

Perfume for sandalwood tone

| Ingredient | Parts by weight |
|---|---|
| Lavandin oil | 110 |

-continued

| Ingredient | Parts by weight |
|---|---|
| Anisaldehyde | 5 |
| Amyl salicylate | 30 |
| Geranium oil | 45 |
| Cinnamic aldehyde | 10 |
| Coumarin | 90 |
| Santalex | 300 |
| Patchouli oil | 60 |
| Perfume composiion obtained in Preparatory Example 4 | 350 |
| | 1000 |

The above described formulation gave a perfume for sandalwood tone having a noble musk tone. The fragrance thereof was greatly improved in comparison with the perfume formulated with the acetylated mixture obtained in Preparatory Example 2 in place of the perfume composition in the above described formulation.

EXAMPLE 2

A perfume described below was prepared by using the 4-acetyl-1,1-[a] compound obtained in Preparatory Example 4.

Perfume for okamoss tone

| Ingredient | Parts by weight |
|---|---|
| α-Amyl cinnamaldehyde | 110 |
| Methyl anthranilate | 10 |
| Eugenol | 40 |
| Aurantiol(Methyl N—3,7-dimethyl-7-hydroxyoctyliden anthranilate) | 10 |
| Phenethyl alcohol | 22 |
| Benzyl acetate | 70 |
| Terpinyl acetate | 70 |
| Verbenone(p-t-Butyl cyclohexyl acetate) | 150 |
| Dihydromyrcenol | 7 |
| p-Cresyl methyl ether | 6 |
| Eucalyptus oil | 30 |
| Lavandin oil | 200 |
| Coumarin | 45 |
| Patchouli oil | 50 |
| Lilial(p-t-Butyl-α-methyl hydro cinnamic aldehyde) | 35 |
| 4-Acetyl-1,1-[a] compound obtained in Preparatory Example 4 | 145 |
| | 1000 |

The above described formulation gave a perfume for chic and deep oakmoss tone. The fragrance thereof was greatly improved in comparison with the perfume formulated with the acetylated mixture obtained in Preparatory Example 2 in place of the 4-acetyl-1,1-[a] compound in the above described formulation.

REFERENCE EXAMPLE 2

Five kinds of the novel compounds obtained in Preparatory Examples 4 and 5 were subjected to the test of primary irritation by open patch, test of photo-toxicity by the Morikawa method and test of sensitizability by the Magnason method using guinea pigs with the hairs shaved off. The results are shown in Table 2.

TABLE 2

| | Primary irritation (24 hours) | | Photo-toxicity (24 hours) | | Sensitization (48 hours) | |
|---|---|---|---|---|---|---|
| | Concentration | | | | | |
| Sample | 10% | 5% | 10% | 5% | 10% | 5% |
| 4-Acetyl-1,1-[a] compound | — | — | — | — | — | — |
| 5-Acetyl-1,1-[a] compound | — | — | — | — | — | — |
| 5-Acetyl-3,3-[a] compound | — | — | — | — | — | — |
| 4-Propionyl-1,1-[a] compound | — | — | — | — | — | — |
| 5-Propionyl-3,3-[a] compound | — | — | — | — | — | — |

(Solvent: acetone; application dose: 0.02 ml)

All of the samples exhibited absolutely no irritation and sensitization to the animal skin to give confirmation that the novel compounds of the present invention were of high safety.

USE IN INDUSTRY

The perfume composition of the present invention has excellent musk fragrance and is a material of high safety. Accordingly, it is used as a perfume base in soaps, perfumes, cosmetic preparations, airfreshners, masking agents and the like.

We claim:

1. A hexahydro-1H-cyclopenta(a)naphthalene compound of the formula

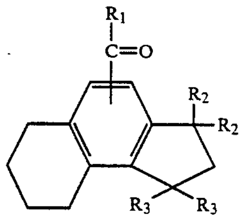

wherein, $R_1$ is a methyl group or an ethyl group and either one of $R_2$ and $R_3$ is a methyl group and the other of $R_2$ and $R_3$ is a hydrogen atom.

2. The compound of claim 1 of the formula

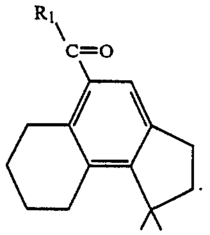

3. The compound of claim 1 of the formula

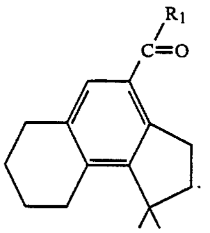

4. The compound of claim 1 of the formula

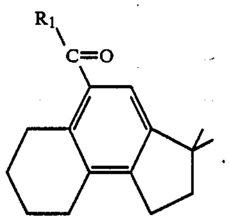

5. The compound of claim 1 of the formula

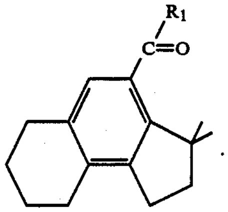

6. A perfumery composition comprising a plurality of odoriferous chemicals together with from 0.001 to 10% by weight of said composition of at least one compound of the formula of claim 1.

7. A perfumery composition comprising a plurality of odoriferous chemicals together with from 0.001 to 10% by weight of said composition of the compound of compound of claim 2.

8. A perfumery composition comprising a plurality of odoriferous chemicals together with from 0.001 to 10% by weight of said composition of the compound of compound of claim 3.

9. A perfumery composition comprising a plurality of odoriferous chemicals together with from 0.001 to 10% by weight of said composition of the compound of compound of claim 4.

10. A perfumery composition comprising a plurality of odoriferous chemicals together with from 0.001 to 10% by weight of said composition of the compound of compound of claim 5.

11. The perfumery composition of claim 6 containing at least three different of said hexahydro-1H-cyclopenta(a)naphthalene compounds in a total amount of from 0.01 to 1% by weight of said composition.

* * * * *